(12) United States Patent
Bartlett, II et al.

(10) Patent No.: US 9,149,581 B2
(45) Date of Patent: Oct. 6, 2015

(54) COMPACT DEVICE FOR RAPIDLY MIXING AND DELIVERING SUBSTANCES TO A PATIENT

(75) Inventors: Rush L. Bartlett, II, Edgeron Street, IN (US); Arthur L. Chlebowski, Granger, IN (US); Peter M. Greco, Jr., Fishers, IN (US); Zachary R. Gosnell, Terre Haute, IN (US); Jared L. West, Liberty Township, IN (US); Barry J. Davignon, Terre Haute, IN (US)

(73) Assignee: GlucaGo LLC, El Segundo, CA (US)

( * ) Notice: Subject to any disclaimer, the term of this patent is extended or adjusted under 35 U.S.C. 154(b) by 438 days.

(21) Appl. No.: 13/255,753

(22) PCT Filed: Mar. 9, 2010

(86) PCT No.: PCT/US2010/026670
§ 371 (c)(1),
(2), (4) Date: Mar. 20, 2012

(87) PCT Pub. No.: WO2010/104858
PCT Pub. Date: Sep. 16, 2010

(65) Prior Publication Data
US 2012/0179137 A1 Jul. 12, 2012

Related U.S. Application Data

(60) Provisional application No. 61/241,462, filed on Sep. 11, 2009, provisional application No. 61/182,835, filed on Jun. 1, 2009, provisional application No. 61/158,435, filed on Mar. 9, 2009.

(51) Int. Cl.
*A61M 5/28* (2006.01)
*A61M 5/24* (2006.01)
(Continued)

(52) U.S. Cl.
CPC .............. *A61M 5/284* (2013.01); *A61M 5/2448* (2013.01); *A61M 5/3202* (2013.01); *A61M 37/00* (2013.01); *A61M 2005/3267* (2013.01)

(58) Field of Classification Search
CPC ... A61M 5/31596; A61M 5/19; A61M 5/002; A61M 2015/0031; A61M 5/284; A61M 5/2448; A61M 5/3302; A61M 37/00; A61M 2005/3267; A61J 1/2093
USPC ............. 604/82–85, 87, 88–89, 91, 200–205, 604/263, 518
See application file for complete search history.

(56) References Cited

U.S. PATENT DOCUMENTS 2,591,706 A   4/1952 Lockhart
(Continued)

FOREIGN PATENT DOCUMENTS

DE   1291859   4/1969
(Continued)

OTHER PUBLICATIONS

Int'l Search Report for PCT/US2011/030910 issued by the U.S. Patent Office as Search Authority, Jun. 9, 2011, 1-2.
(Continued)

*Primary Examiner* — Theodore Stigell
*Assistant Examiner* — Lauren M Peng
(74) *Attorney, Agent, or Firm* — Dorsey & Whitney LLP (57) ABSTRACT

Injection devices are disclosed for injections of substances. The disclosed devices separately may hold two separate substances, e.g., solid, liquid or gas substances, in separate compartments which are interrupted so that the separate substances come into contact during the activation of the device. One disclosed device includes a needle for injection and two substances that are mixed with only a few actions by the operator of the device. The device may or may not activate mixing by the removal of a sleeve which triggers compartment interaction through movement of pins, pegs, springs, wires, string, or other mechanisms which allow the materials held in separate chambers to come into contact with each other. Operator error during mixing and checking the dosage of substances to be injected is avoided with the disclosed devices. Also, the needle is maintained in a sterile state because the needle is held internally of the device until the sleeve is removed and the device begins to activate.

20 Claims, 8 Drawing Sheets

(51) Int. Cl.
*A61M 5/32* (2006.01)
*A61M 37/00* (2006.01)

(56) References Cited

U.S. PATENT DOCUMENTS

| | | | |
|---|---|---|---|
| 2,869,543 A * | 1/1959 | Ratcliff et al. | 604/90 |
| 3,380,451 A | 4/1968 | Porter et al. | |
| 3,678,931 A | 7/1972 | Cohen | |
| 3,699,961 A | 10/1972 | Szpur | |
| 3,785,379 A | 1/1974 | Cohen | |
| 3,838,689 A | 10/1974 | Cohen | |
| 3,885,710 A | 5/1975 | Cohen | |
| 3,939,833 A | 2/1976 | Hansson et al. | |
| 4,031,892 A | 6/1977 | Hurschman | |
| 4,059,109 A | 11/1977 | Tischlinger | |
| 4,061,144 A | 12/1977 | Strickman et al. | |
| 4,215,701 A | 8/1980 | Raitto | |
| 4,715,854 A | 12/1987 | Vaillancourt | |
| 4,921,491 A | 5/1990 | Champ | |
| 5,279,606 A | 1/1994 | Haber et al. | |
| 5,352,196 A | 10/1994 | Haber et al. | |
| 5,377,689 A | 1/1995 | Mercereau | |
| 5,433,705 A * | 7/1995 | Giebel et al. | 604/82 |
| 5,562,631 A * | 10/1996 | Bogert | 604/192 |
| 5,620,423 A | 4/1997 | Eykmann et al. | |
| 5,630,796 A * | 5/1997 | Bellhouse et al. | 604/518 |
| 5,752,940 A | 5/1998 | Grimard | |
| 5,779,668 A | 7/1998 | Grabenkort | |
| 5,785,683 A | 7/1998 | Szapiro et al. | |
| 5,817,055 A | 10/1998 | Ljungquist | |
| 5,971,953 A | 10/1999 | Bachynsky | |
| 6,001,080 A | 12/1999 | Kuracina et al. | |
| 6,001,089 A | 12/1999 | Burroughs et al. | |
| 6,602,223 B2 | 8/2003 | Szapiro et al. | |
| 2002/0168530 A1 | 11/2002 | Tingey et al. | |
| 2003/0100921 A1 | 5/2003 | Addis et al. | |
| 2004/0186432 A1 | 9/2004 | Barry et al. | |
| 2006/0178638 A1 | 8/2006 | Reynolds | |
| 2008/0234654 A1 | 9/2008 | McCarthy et al. | |
| 2008/0319400 A1 | 12/2008 | Thorne, Jr. et al. | |
| 2009/0036864 A1 | 2/2009 | Moy et al. | |
| 2009/0062740 A1 | 3/2009 | Thorne, Jr. | |
| 2009/0247957 A1 | 10/2009 | Heutschi | |
| 2009/0254035 A1 * | 10/2009 | Kohlbrenner et al. | 604/135 |
| 2010/0168712 A1 | 7/2010 | Tuckwell et al. | |
| 2011/0106021 A1 | 5/2011 | Ruegg et al. | |
| 2012/0209171 A1 | 8/2012 | Vedrine et al. | |

FOREIGN PATENT DOCUMENTS

| | | |
|---|---|---|
| EP | 0112574 | 7/1984 |
| EP | 0340899 A2 | 11/1989 |
| EP | 0511402 A1 | 11/1992 |
| JP | 09-225032 | 9/1997 |
| WO | WO 2007131013 A1 * | 11/2007 |
| WO | 2010/139793 | 12/2010 |

OTHER PUBLICATIONS

Oct. 22, 2013 International Search Report for PCT/US2013/038490 issued by the European Patent Office as Searching Authority, Oct. 22, 2013 pp. 1-7.

Oct. 8, 2013 International Search Report for PCT/US2013/047935 issued by the Korean Patent Office as Searching Authority, Oct. 8, 2013 pp. 1-3.

Oct. 8, 2013 Written Opinion for PCT/US2013/047935 issued by the Korean Patent Office as Searching Authority, Oct. 8, 2013, pp. 1-8.

Mar. 19, 2013 International Search Report for PCT/US2012/056318 issued by the Korean Patent Office as Search Authority, Mar. 19, 2013 pp. 1-3.

Jun. 9, 2011 International Search Report for PCT/US2011/030910 issued by the United States Patent Office as Search Authority, Jun. 9, 2011 pp. 1-2.

* cited by examiner

COMPACT DEVICE FOR RAPIDLY MIXING AND DELIVERING SUBSTANCES TO A PATIENT

BACKGROUND

1. Technical Field

Devices are disclosed for rapidly mixing and delivering substances, such a lyophilized or spray dried substances. For example, devices are disclosed for rapidly mixing and injecting solid stored substances, such as glucagon, vaccines, animal products, combat medications, antibodies, recombinant proteins, anti-venoms, vitamins, drugs, compounds, and many others, for use in many different types of therapies and treatments are possible. Methods of rapidly treating hypoglycemia and other conditions are also disclosed.

2. Description of the Related Art

Diabetes mellitus affects over 24 million Americans and is the seventh leading cause of death nationally. Approximately 17.9 million diabetics have been diagnosed in the United States. Diabetes can take two forms: Types I and II. Type I patients cannot produce insulin while Type II patients suffer from impaired glucose regulatory pathways or insulin production. Both Types I and II patients require treatment with insulin injections, lifestyle changes, monitoring, or oral medications.

Hypoglycemia is a condition of lower than normal blood sugar that results in a lifestyle of a diabetic patient. Hypoglycemia can result in coma, seizure, or even death in 2-4% of diabetics. Decreased levels of glucose can have damaging effects on the brain or other organs. The incidence of hypoglycemia in the diabetic population is hard to measure because so many the level of hypoglycemia amongst diabetics varies. Usually, a type I diabetic experiences a severe hypoglycemia episode at least once per year and mild episodes several times per week, Type II diabetics have a 20% chance of having a severe attack sometime during their life but also have mild episodes in higher frequencies. A blood glucose level below 50 mg/dL is considered a severe episode of hypoglycemia. However, as patients age, some lose their ability to recognize symptoms.

Diabetics currently only have two options to treat severe hypoglycemia. Both options are hypoglycemic rescue kits manufactured by Nova Nordisk and Eli Lilly. These kits comprise a single needle filled with a sterile solution, and a vial of glucagon/lactose powder which is mixed to and injected into the patient by hand. This method is dangerous and not effective for a wide number of potential users who are unfamiliar with needles, or have trouble focusing on the need to mix the powder and liquid during the stress of an attack on themselves or a person whom they are assisting in an emergency.

Accordingly, improved devices and methods for conveniently and quickly delivering medical products to a patient are needed.

SUMMARY OF THE DISCLOSURE

Injection devices are disclosed that mix and inject substances such as, but not limited to, glucagon, epinephrine, anti-venoms, heart attack rescue reagents, drugs, solid compounds, powdered compounds, liquid compounds, antibodies, vitamins, nucleic acids, proteins, peptides, etc. The disclosed devices separately may hold two separate substances, e.g., solid, liquid or gas substances, in separate compartments which are interrupted so that the separate substances come into contact during the activation of the device. One disclosed device includes a needle for injection and two substances that are mixed with only a few actions by the operator of the device. The device may or may not activate mixing by the removal of a sleeve which triggers compartment interaction through movement of pins, pegs, springs, wires, string, or other mechanisms which allow the materials held in separate chambers to come into contact with each other.

Operator error during mixing and checking the dosage of substances to be injected is avoided with the disclosed devices. Also, the needle is maintained in a sterile state because the needle is held internally of the device until the sleeve is removed and the device begins to activate.

The disclosed devices can be used to mix and inject two or more substances into a patient or inject a single substance without mixing. The substances may be solid, liquid or gas substances and can be used for, but not limited to, injection of vaccines, proteins, peptides, vitamins, drugs, substances, compounds, nano particles, devices, etc. The disclosed devices will allow simple administration with minimal interaction on the part of the user taken place suggested but not limited to the removal of the sleeve of the device and then compression at the desired site of injection causing the mechanism of action to mix and inject the substances. The removal of the sleeve may cause the mixing as illustrated in three of the designs below, or the sleeve may merely protect the mechanism from preliminary injection or unsterile contamination.

As a general example, for the case of glucagon injection, glucagon will be held in a lyophilized form in one compartment. Then the sleeve of the device is removed and the device is used by the patient causing the mixing of the glucagon with a solvent and then subsequent injection into the patient there by raising the blood glucose level of the patient as a possible treatment of a hypoglycemic attack. The mechanisms may or may not be designed as to indicate an expired device, a used device, a malfunctioning device, or may or may not also retract the needle into the device as to cover it from secondary puncture after use. The advantages of separate chambers for the substances increase the shelf life of the substances.

In one design, a disclosed device comprises a sleeve which is removed prior to use causing a thin component to be pulled through the device to activate mixing of the substances to be injected. Then the sleeve is fully removed and the device is ready for compression. In the front housing of the device the front of a needle is positioned between two membranes which hold a liquid reservoir in front of the needle as to help keep the needle primed with liquid for use prior to injection into the skin. Also, the device may inject without having the extra need for a shell because the device locks and then moves to the inner component of the device to serve as an activating mechanism for the plunger which then helps to expel the contents of the device out the end of the needle and into a patient. Once the device is used it may or may not indicate that it has been used and it may or may not have a spring in the front compartment of the device or other mechanism elsewhere which causes the needle to be retracted all or partially into the housing of the device as to help prevent secondary injury from the exposed needle.

In one embodiment, a disclosed device for mixing at least two substances to form a mixture and for delivering the mixture to a patient comprises a first chamber in communication with a dispense outlet. The first chamber accommodates a first substance and a second chamber accommodates a second substance. The second chamber is isolated from the first chamber by a barrier. The barrier coupled to a sleeve. Wherein, movement of the sleeve under manual pressure causes the barrier to become dislodged and the first and second substances to mix in at least one of the first and second chambers.

In a refinement, the dispense outlet is a cannula.

In a refinement, the second substance is a powder.

In a refinement, the first substance is a liquid.

In a refinement, the first substance of the first chamber is a liquid of the second substance of the second chamber is a powder.

In a refinement, the first chamber is disposed between the sleeve and the second chamber.

In a refinement, the second chamber is disposed between the upper housing and the barrier.

In a refinement, the barrier is a piece of foil or material that is easily torn, broken, or moved.

In a refinement, the barrier may coupled to the sleeve by a coupling element that passes through the cannula. In such a refinement, the coupling element may a line.

In a refinement, the barrier is coupled to the sleeve by a coupling element selected from the group consisting of a string, a line, a wire and combinations thereof.

In a refinement, one of the first and second substances is a solvent and the other of the first and second substances is selected from the group consisting of glucagon, epinephrine, heart attack rescue reagents, drugs, solid compounds, antivenoms, antibodies, powdered compounds, liquid compounds, vitamins, nucleic acids, proteins, peptides, and combinations thereof.

In a refinement, the device comprises at least one housing in which the first and second chambers are disposed. The at least one housing comprises a window for exposing the barrier.

In a refinement, the barrier may be a plug.

In a refinement, the sleeve is coupled to a lower housing. The plug is disposed between the first and second chambers in an upper housing. The lower and upper housings are slidably and telescopically coupled together, wherein movement of the sleeve and lower housing with respect to the upper housing causing dislodgment of the plug and allowing the first and second substances to mix.

Methods for mixing at least two substances to form a mixture and for delivering the mixture to a patient are also disclosed. One disclosed method comprises providing a device in accordance with claim 1 wherein the dispense outlet is a cannula, moving the sleeve under manual pressure causing the barrier to become dislodged and the first and second substances to mix and form a mixture in at least one of the first and second chambers, and injecting the mixture into the patient through the cannula.

Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiments illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

Turning first to FIGS. 1-9, the device 30 is disclosed which comprises an outer sleeve or cap 31 that may include an open end 32 covered by an end cap 33 that, in this example, includes an eyelet 34 that facilitates removal of the sleeve 31 from the lower and upper housings 35, 36. The lower housing 35 accommodates a spring or biasing member 37 and a needle or cannula 38. In the embodiment illustrated in FIGS. 1-9, the end cap 33 and sleeve 31 are coupled to or otherwise connected to a barrier 39. The barrier 39 separates a first chamber 41 from a second chamber 42. In one embodiment, the first chamber 41 accommodates a liquid, such as saline, and the second chamber 42 accommodates a powdered material, such as glucagon, antibodies, or a vaccine. Other examples will be apparent to those skilled in the art and are too numerous to mention here.

Figure 1:
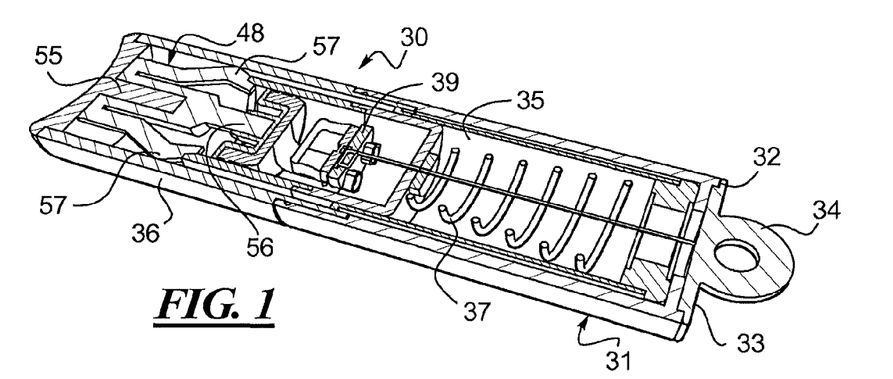
FIG. 1 is a sectional and perspective view of a disclosed device for mixing two substances and delivering the mixture in the form of an injection.
Figures 2, 3:
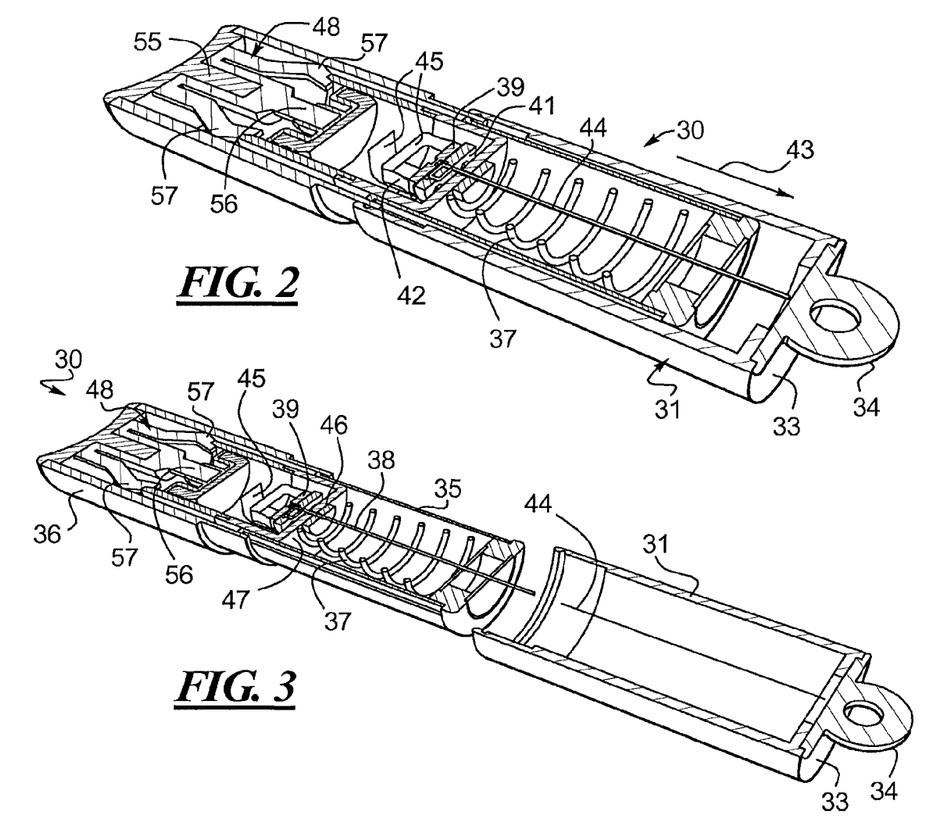
FIG. 2 is another sectional perspective view of the device shown in FIG. 1 illustrating the removal of the outer sleeve which applies tension to the barrier between the two chambers by way of the outer sleeve being connected, coupled or tethered to the barrier by a string, line or other thin coupling element.
FIG. 3 is another perspective and sectional view of the device illustrated in FIGS. 1-2, particularly illustrating the sleeve and string detached from the barrier layer thereby enabling mixing of the substances into two chambers.

FIG. 2 illustrates the sleeve 31 and end cap 33 being pulled in the direction of the arrow 43. As illustrated in FIGS. 2 and 3, the end cap 33 is coupled to the barrier 39 by the coupling element 44 which, in this case, is a string or line. As the sleeve 31 and end cap 33 are pulled in the direction of the arrow 43, stress is imposed on the barrier 39 by the coupling element 44. In one embodiment, the barrier 39 comprises a piece of foil that may be torn or another suitable barrier material susceptible to tearing or rupture. When the foil barrier 39 is torn, powder in the second chamber 42 is exposed to liquid in the first chamber 41 and the mixing begins. Additional mixing element(s) 45 may be provided to enhance the mixing of the powder and liquid from the chambers 42 and 41 into a homogeneous mixture suitable for injection. In one embodiment, the mixing element(s) may be in the form of a film, such as a polymer film.

As illustrated in FIG. 3, the cannula 38 may provide a convenient path for the coupling element 44 to extend from the end cap 33 to the barrier 39. Both the cannula 38 and string or coupling element 44 extend through the membrane 46 that is supported by the cross frame 47.

Figure 4:
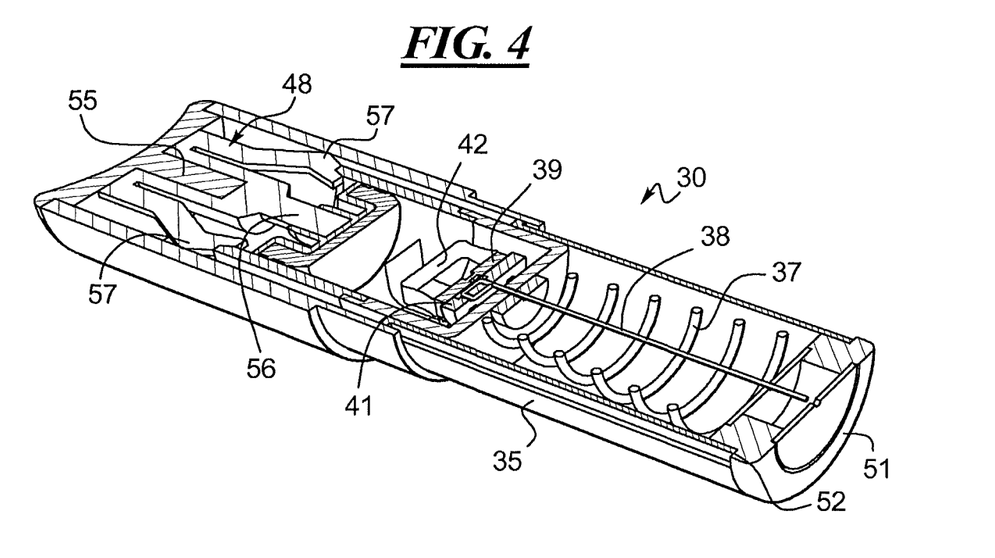
FIG. 4 is another perspective and sectional view of the device illustrated in FIGS. 1-3 without the sleeve.
Figure 5:
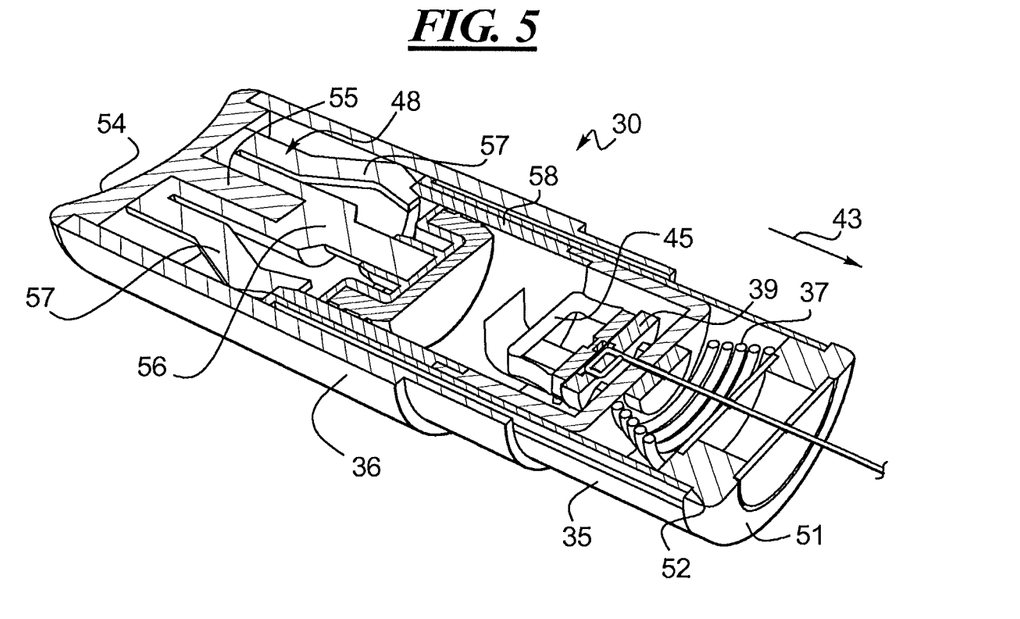
FIG. 5 is another perspective and sectional view illustrating the compression of the spring and lower housing telescopically into the upper housing and may or may not prime the needle.
Figure 6:
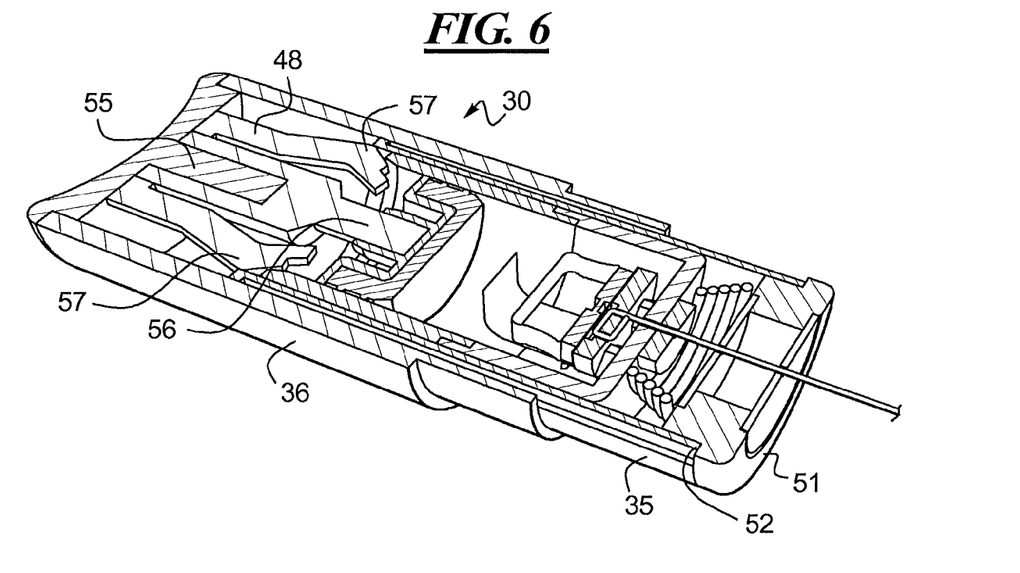
FIG. 6 is another perspective and sectional view of the device illustrated in FIGS. 1-5 illustrating the compression of the upper housing telescopically over the lower housing as the device is ready to inject the mixture into a patient.
Figure 7:
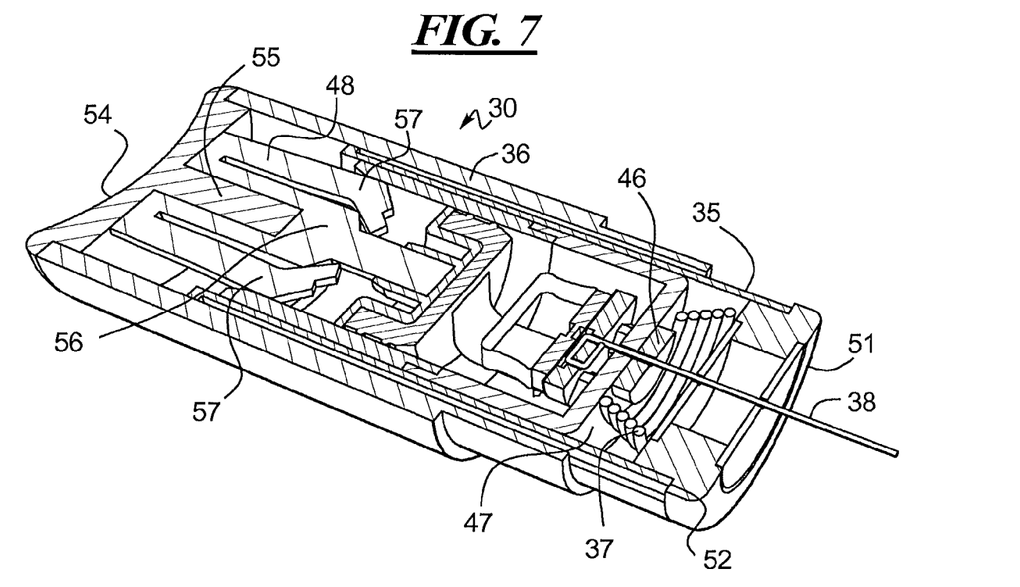
FIG. 7 is another sectional perspective view of the device illustrated in FIGS. 1-6 with the injection progress.
Figure 8:
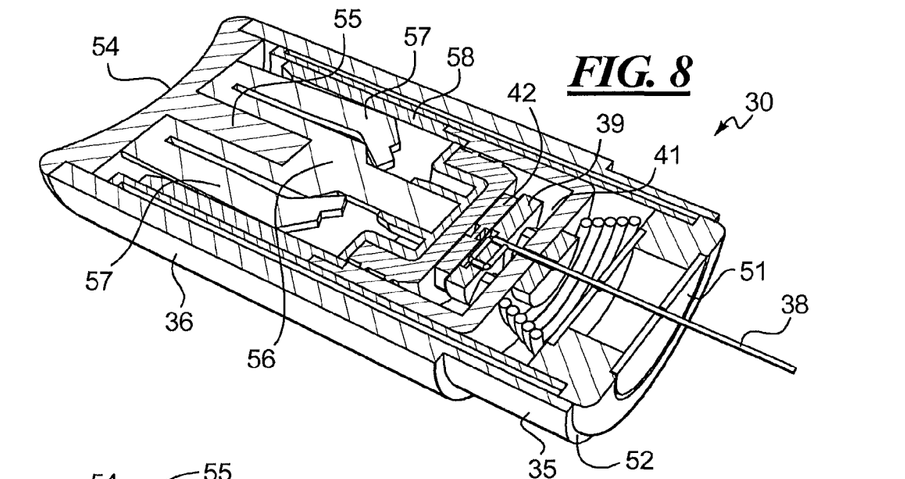
FIG. 8 is another sectional perspective view of the device illustrated in FIGS. 1-7 with the injection completed.
Figure 9:
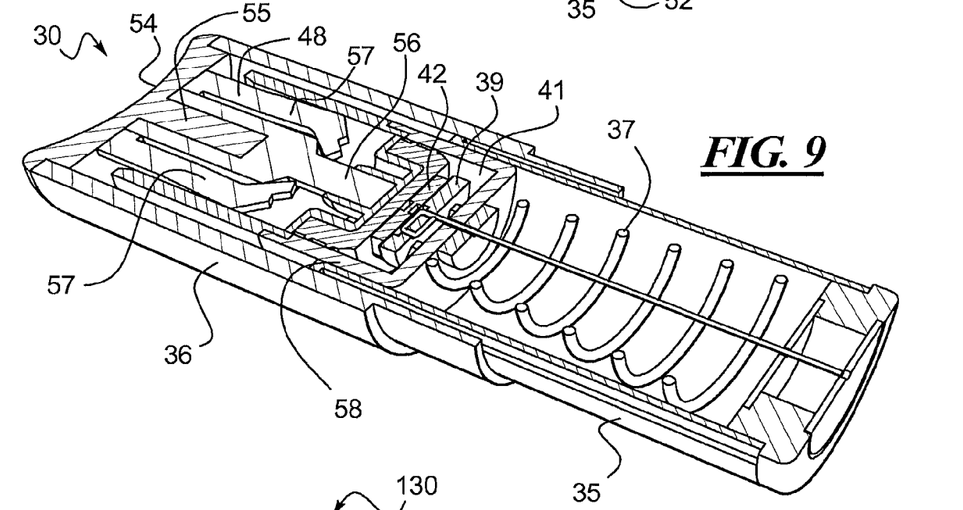
FIG. 9 illustrates a spent or used device as disclosed in FIGS. 1-8 with the needle retracted back into the lower housing and ready for recycling or discard.
Figure 10:
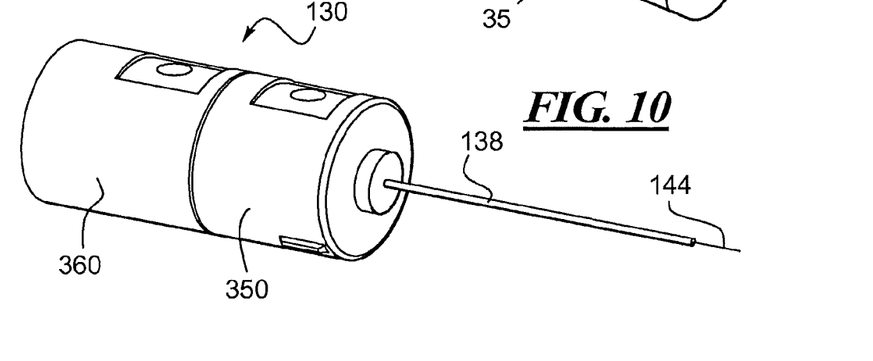
FIG. 10 is a perspective view of yet another disclosed device for mixing two substances injecting the mixture into a patient.

FIG. 4 illustrates the device 30 with the sleeve 31 and coupling element 44 removed and the barrier 39 damaged, torn or ruptured so that materials from the chambers 41 and 42 are being mixed. The mixture of materials from the chambers 41, 42 is now ready to be injected. FIG. 5 illustrates the compression of the lower housing 35 into the upper housing 36 and the compression of the spring 37. FIG. 6 illustrates the compression of the upper housing 36 over the lower housing 35 and the compression or loading of the secondary biasing member 48. In FIG. 6, the device 30 is fully loaded and ready for an injection which is illustrated in FIGS. 7-8. The secondary biasing member 48 is connected to the second chamber 42 by the end wall 54 which includes a post 55 that is frictionally received by the center post 56 of the secondary biasing member 48. As the device 30 is compressed into the position illustrated in FIG. 6, the outer legs 57 of the biasing member 48 become loaded for purposes of biasing the central housing 58 and lower housing 35 in the direction of the arrow 43. This action is illustrated sequentially in FIGS. 6-8. In FIG. 9, the biasing elements 37, 48 are fully extended and the cannula 38 has become retracted within the lower housing 35. FIGS. 5-9 also illustrate the end plug 51 which covers the open end 52 of the lower housing 35. Preferably, the end plug 51 is equipped with a membrane through which the cannula 38 passes.

Figure 11:
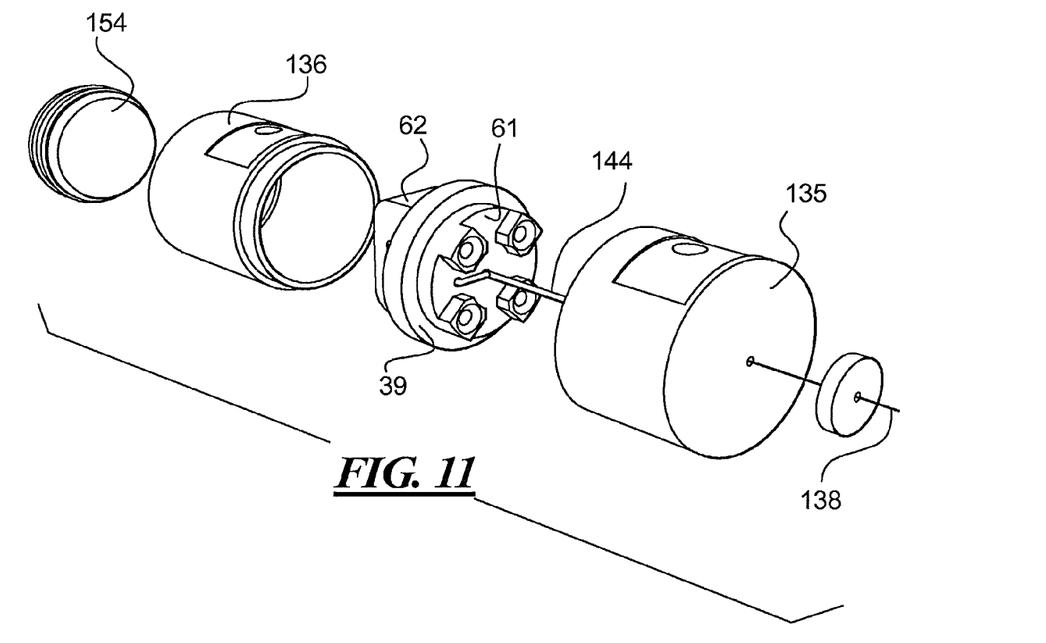
FIG. 11 is a perspective and exploded view of the device illustrated in FIG. 10.
Figure 12:
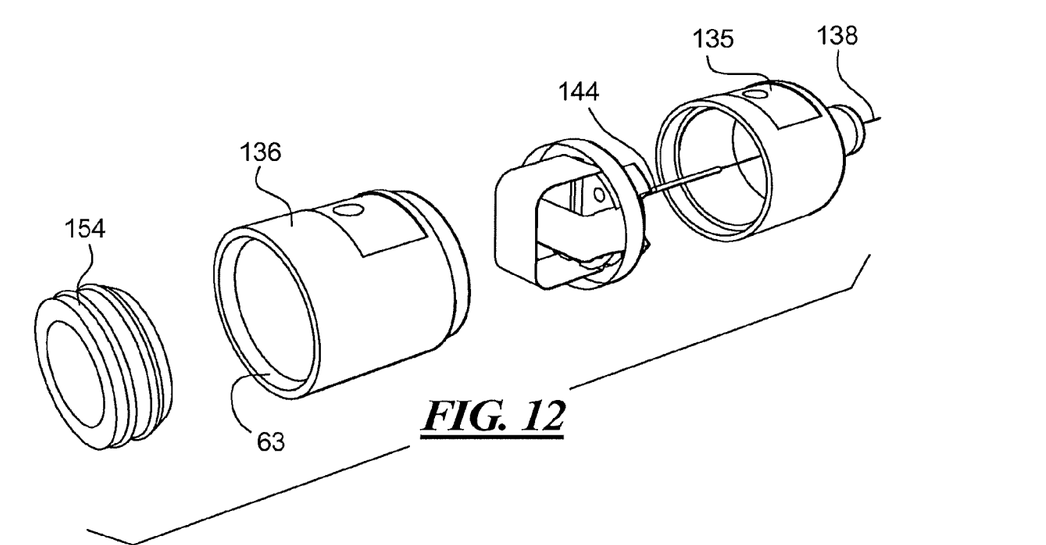
FIG. 12 is another perspective and exploded view of the device illustrated in FIGS. 10-11.
Figure 13:
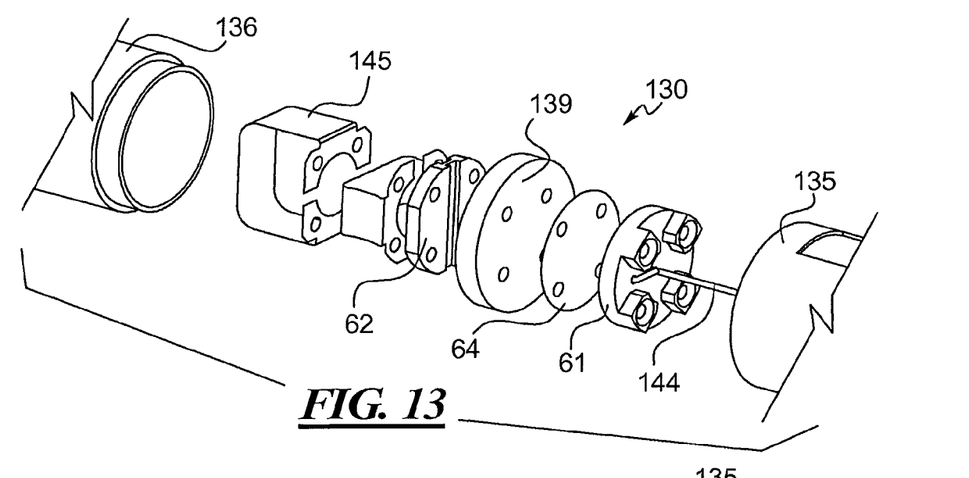
FIG. 13 is a partial perspective and exploded view of the device illustrated in FIGS. 10-12.
Figure 14:
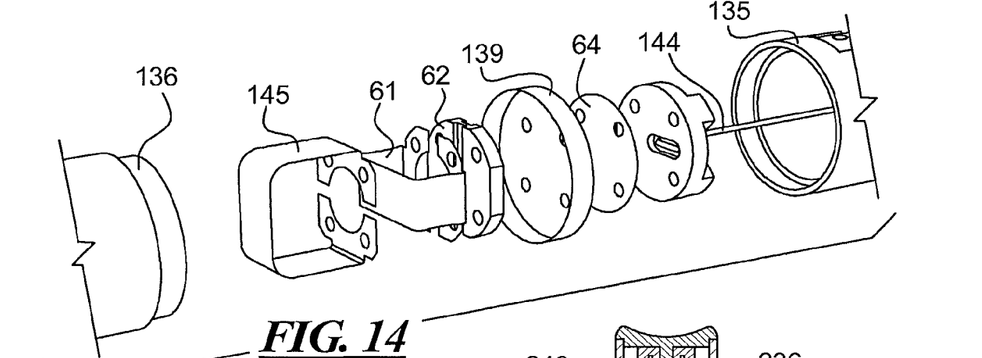
FIG. 14 is another partial and perspective view of the device illustrated in FIGS. 10-13.

FIGS. 10-14 illustrate yet another embodiment 130. The device 130 includes an upper housing 136, lower housing 135 and cannula 138. As illustrated in FIG. 11, a coupling element 144 is connected to the barrier 139. In the embodiment 130 illustrated in FIGS. 10-14, the barrier 139 includes a pair of plates 61, 62 for purposes of imposing a shear force on the foil barrier 139. The open end 63 of the upper housing 136 is covered by the end plug 154. Mixing elements 145 may also be provided to move powder from above the foil barrier 139 two below the foil barrier 139 or towards the right in the orientation of FIGS. 13 and 14. The foil barrier 139 may be equipped with the plates 61, 62 as discussed above and an additional one or more polycarbonate films 64 (FIGS. 13-14) may be included for purposes of allowing the foil barrier 139 and foil plates 61, 62 to flex.

In operation, the coupling element 144 may be coupled to a protective sleeve or cap (not shown). Tension applied to the coupling element 144 will be translated to the barrier 139, which eventually tears or ruptures. The powder in the second chamber disposed opposite the barrier 139 from the lower housing 135 is then mixed with liquid disposed in the first chamber disposed opposite the barrier 139 from the upper housing 136.

Figure 15:
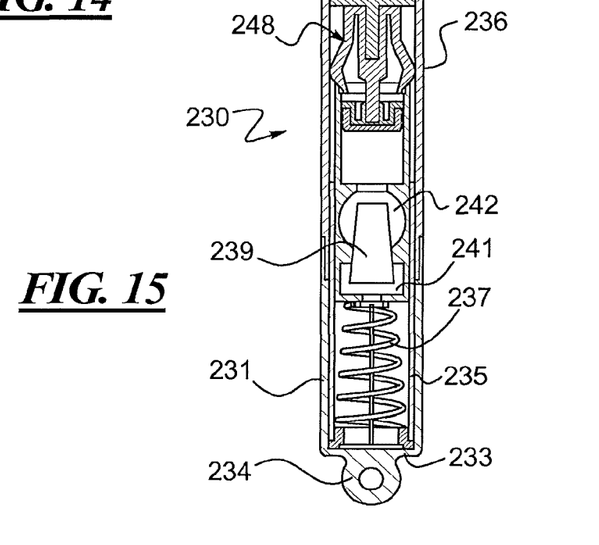
FIG. 15 is a front a sectional view illustrating yet another disclosed device that includes a dislodgeable stopper that prevents premature mixing of the two substances and the use of two chambers for the liquid substance disposed on either side of a chamber for a powdered substance.
Figure 16:
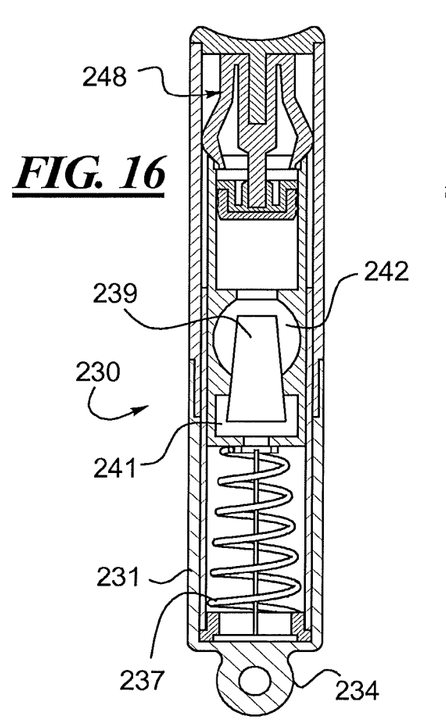
FIG. 16 is another front sectional view of the device illustrated in FIG. 15.
Figure 17:
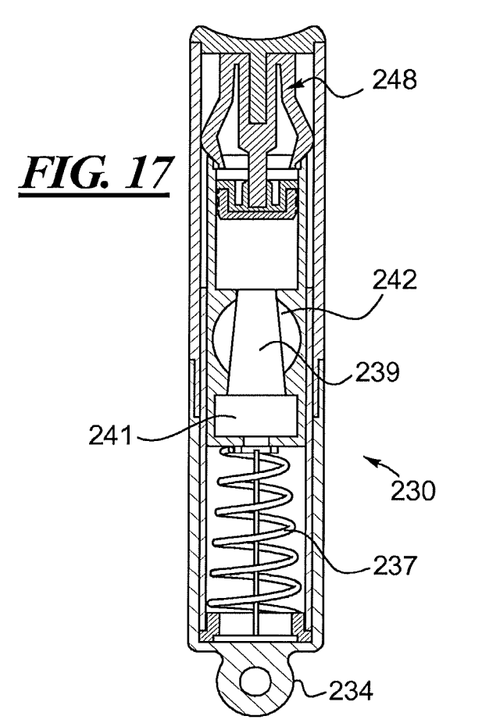
FIG. 17 is yet another front sectional of the device illustrated in FIGS. 16-17.
Figure 18:
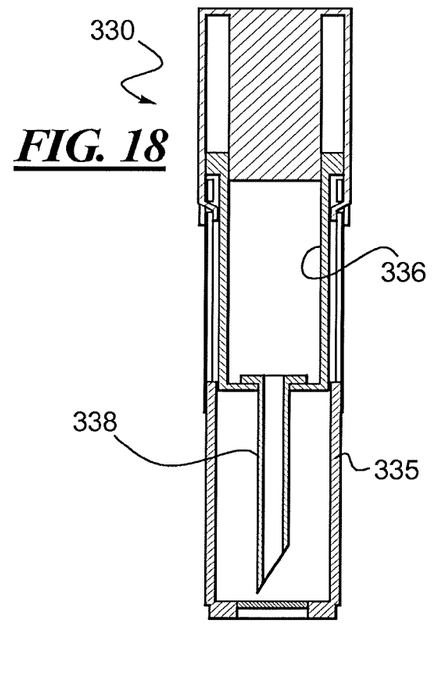
FIG. 18 is a front sectional view of a disclosed device which does not include two separate chambers for mixing two substances, but which provides a rapid means for injecting a solution into a patient experiencing an emergency.
Figure 19:
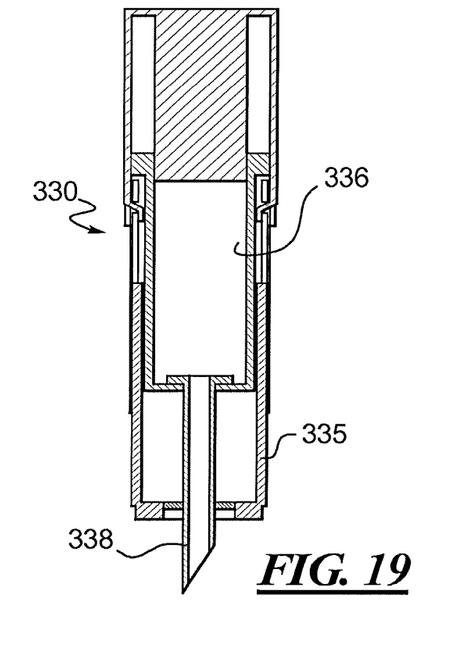
FIG. 19 is another front sectional view of the device illustrated in FIG. 18 at the beginning of an injection.
Figures 20, 21:
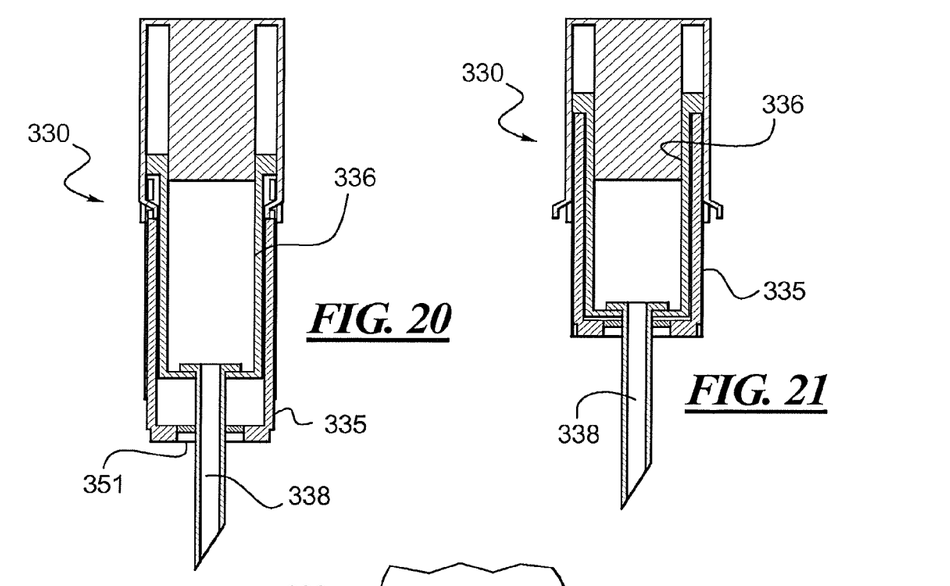
FIG. 20 is another front sectional view of the device illustrated in FIG. 18 at the beginning of an injection.
FIG. 21 is another front sectional view of the device illustrated in FIGS. 18-20 with the injection in progress.
Figures 22, 23, 24:
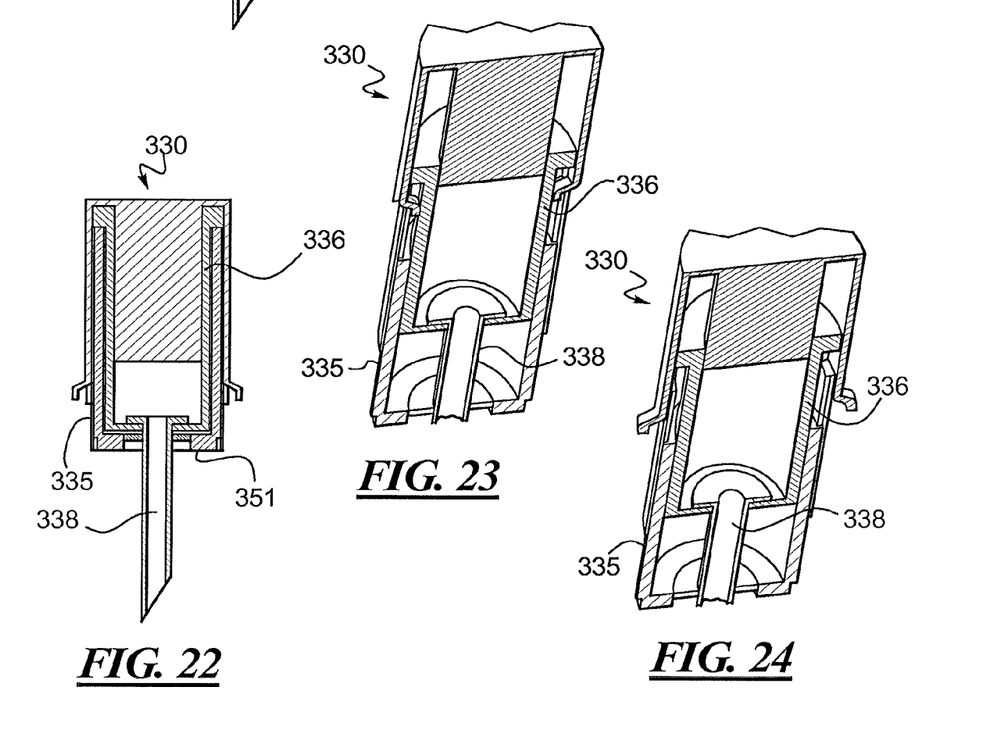
FIG. 22 is another front sectional view of the device illustrated in FIGS. 18-21 as an injection is completed.
FIG. 23 is a bottom perspective view of the device illustrated in FIGS. 18-22.
FIG. 24 is another bottom perspective view of the device illustrated in FIGS. 18-23.

As shown in FIGS. 15-17, a coupling element 44 (FIGS. 1-9) or 144 (FIGS. 10-14) extending between a removable item such as a sleeve or cap 31 or other handle is not necessary. For example, any type of movable or disruptable barrier disposed between the first and second chambers 41, 42 or 241, 242 may be employed. In FIGS. 15-17, the movable barrier is provided in the form of a plug 239. While the two embodiments illustrated in FIGS. 1-9 and 10-14 disclose foil barriers 39, 139 other impermeable or relatively impermeable barriers will be apparent to those skilled in the art including, but not limited to, other metallic barriers or membranes and non-metallic barriers or membranes such as polymer barriers or membranes.

Turning to FIGS. 15-17, an additional device to 30 is illustrated which includes a conical plug 239 that serves as a barrier between the first chamber 241 and second chamber 242. As seen in the sequence illustrated in FIGS. 15-17, as the device 230 is compressed, the plug 239 extends upward towards the secondary biasing element 248 thereby establishing communication between the lower and second chambers 241, 242. Otherwise the device 230 is similar in construction to the device 30 illustrated in FIGS. 1-9 as it includes a spring 237, upper and lower housings 236, 235, an end cap 233, sleeve 231, eyelet 234 and secondary biasing member 248.

While FIGS. 15-17 illustrate a conical plug 239, the shape of the plug to 39 is relatively unimportant. Dislodgment of the plug from its position between the first and second chambers 241, 242 (compare FIGS. 16 and 17) upon the application of manual pressure is a primary function of the plug 239. For that matter, the application of manual pressure can be used to tear, damage or remove either one of the foil barriers 39, 139 disclosed above in FIGS. 1-14.

FIGS. 18-24 illustrate a single chamber device 330 which includes a lower housing 335 and an upper housing 336. The upper housing 136 includes the single chamber in communication with the cannula 338. As the device 330 is compressed, the cannula extends through the end cap 351 for injecting as illustrated sequentially in FIGS. 19-22. The embodiment illustrated in FIGS. 18-24th is intended for applications where mixing of two different substances is not necessary.

While only certain embodiments have been set forth, alternatives and modifications will be apparent from the above description to those skilled in the art. These and other alternatives are considered equivalents and within the spirit and scope of this disclosure and the appended claims.

The invention claimed is:

1. A device for injecting a substance into a patient, the device comprising:
   an upper housing having an open distal end and a closed proximal end;
   a central housing telescopically within the upper housing at its open distal end;
   a lower housing telescopically coupled with the upper housing at its open distal end and the central housing to form at least one chamber for containing the substance, wherein the at least one chamber comprises:
      a first chamber in fluid communication with the needle, the first chamber accommodating a first substance, and
      a second chamber accommodating a second substance;
   a first biasing element disposed in the lower housing, configured to store compressive force when the upper housing and the lower housing are manually compressed together and to move the upper housing and the lower housing apart from one another when the upper and lower housings are released from compression;
   a second biasing element disposed in the upper housing, configured to substantially resist compression of the upper and central housings until the upper and lower housings are substantially manually compressed together;
   a needle in fluid communication with the at least one chamber and extending into the lower housing such that, when the upper housing and the lower housing are manually compressed together, a distal end of the needle extends out of a distal end of the lower housing for injecting the substance into the patient; and
   a barrier for isolating the second chamber from the first chamber, wherein the barrier may be compromised under manual pressure causing the first and second substances to mix in at least one of the first and second chambers,
   wherein the first biasing element is configured to move the upper housing and the lower housing apart, when they are released from compression, to retract the distal end of the needle fully into the lower housing,
   wherein the lower housing and the upper housing are configured to telescope toward one another only by manual force;
   wherein the central housing and the upper housing are configured to telescope toward one another by manual force; and
   wherein the barrier is coupled to a sleeve by a coupling element that passes through the needle, and wherein movement of the sleeve under manual pressure dislodges the barrier.

2. The device of claim 1, wherein the second substance is a powder.

3. The device of claim 1, wherein the first substance is a liquid.

4. The device of claim 1, wherein the first substance of the first chamber is a liquid and the second substance of the second chamber is a powder.

5. The device of claim 1, wherein the lower housing comprises an open proximal end and a closed distal end, wherein the device further comprises a sleeve removably disposed over the closed distal end of the lower housing.

6. The device of claim 5, wherein the closed distal end of the lower house comprises a membrane through which the distal end of the needle passes.

7. The device of claim 1, wherein the barrier is a piece of foil.

8. The device of claim 7 wherein the barrier is coupled to a sleeve by a coupling element.

9. The device of claim 8 wherein the coupling element is a line.

10. The device of claim 9, wherein the line passes through the needle.

11. The device of claim 1, wherein the coupling element is selected from the group consisting of a string, a line, a wire and combinations thereof.

12. The device of claim 1, wherein the substance is selected from the group consisting of glucagon, epinephrine, heart attack rescue reagents, drugs, solid compounds, powdered compounds, liquid compounds, lipids, sugars, steroids, hormones, vitamins, nucleic acids, vaccines, anti-venoms, antibodies, proteins, peptides, nano-particles and combinations thereof.

13. The device of claim 1, wherein the first biasing member comprises a spring.

14. A device for injecting a substance into a patient, the device comprising:
   an upper housing having an open distal end and a closed proximal end;
   a lower housing telescopically coupled with the upper housing at its open distal end to form at least one chamber for containing the substance, the at least one chamber comprising a first chamber in fluid communication with the needle, the first chamber accommodating a first substance, and a second chamber accommodating a second substance;
   a biasing element disposed in the lower housing, configured to store compressive force when the upper housing and the lower housing are manually compressed together and to move the upper housing and the lower housing apart from one another when the upper and lower housings are released from compression;
   a needle in fluid communication with the at least one chamber and extending into the lower housing such that, when the upper housing and the lower housing are manually compressed together, a distal end of the needle extends out of a distal end of the lower housing for injecting the substance into the patient; and
   a barrier for isolating the second chamber from the first chamber, wherein the barrier may be compromised under manual pressure causing the first and second substances to mix in at least one of the first and second chambers;
   wherein the barrier is a piece of foil coupled to a sleeve by a coupling element,
   wherein the coupling element is a line that passes through the needle,
   wherein the biasing element is configured to move the upper housing and the lower housing apart, when they are released from compression, to retract the distal end of the needle fully into the lower housing, and
   wherein the lower housing and the upper housing are configured to telescope toward one another only by manual force.

15. A device for injecting a substance into a patient, the device comprising:
   an upper housing having an open distal end and a closed proximal end;
   a lower housing telescopically coupled with the upper housing at its open distal end to form at least one chamber for containing the substance, the at least one chamber comprising a first chamber in fluid communication with the needle, the first chamber accommodating a first substance, and a second chamber accommodating a second substance;

a biasing element disposed in the lower housing, configured to store compressive force when the upper housing and the lower housing are manually compressed together and to move the upper housing and the lower housing apart from one another when the upper and lower housings are released from compression;

a needle in fluid communication with the at least one chamber and extending into the lower housing such that, when the upper housing and the lower housing are manually compressed together, a distal end of the needle extends out of a distal end of the lower housing for injecting the substance into the patient; and a barrier for isolating the second chamber from the first chamber, wherein the barrier may be compromised under manual pressure causing the first and second substances to mix in at least one of the first and second chambers, wherein the barrier is coupled to a sleeve by a coupling element that passes through the needle, and wherein movement of the sleeve under manual pressure dislodges the barrier, wherein the biasing element is configured to move the upper housing and the lower housing apart, when they are released from compression, to retract the distal end of the needle fully into the lower housing, and wherein the lower housing and the upper housing are configured to telescope toward one another only by manual force.

16. The device of claim 15, wherein the coupling element is selected from the group consisting of a string, a line, a wire and combinations thereof.

17. A method for injecting a substance into a patient, the method comprising:

manually compressing a lower housing and an upper housing of an injection device telescopically together to compress a biasing member housed in the lower housing and to advance a distal end of a needle of the injection device out of a distal end of the lower housing;

further manually compressing the lower housing and the upper housing together to inject the substance into the patient;

releasing the lower housing and the upper housing from compression to allow the biasing member to automatically move the housings away from one another and thus retract the distal end of the needle into the lower housing; and removing a sleeve from a distal end of the lower housing before the distal end of the needle is advanced out of the distal end of the lower housing, wherein removing the sleeve dislodges a foil barrier between two chambers in the injection device to allow first and second substances housed in the two chambers to mix and form the substance that is injected through the needle into the patient, and wherein the barrier is coupled to the sleeve by a coupling element that passes through the needle.

18. The method of claim 17, wherein the substance is selected from the group consisting of glucagon, epinephrine, heart attack rescue reagents, drugs, solid compounds, powdered compounds, liquid compounds, lipids, sugars, steroids, hormones, vitamins, nucleic acids, vaccines, anti-venoms, antibodies, proteins, peptides, nanoparticles and combinations thereof.

19. The method of claim 17, further comprising advancing the distal end of the needle into the patient before further manually compressing the lower and upper housings together to inject the substance.

20. A device for injecting a substance into a patient, the device comprising:

an upper housing having an open distal end and a closed proximal end;

a lower housing telescopically coupled with the upper housing at its open distal end to form at least one chamber for containing the substance, the at least one chamber comprising a first chamber in fluid communication with the needle, the first chamber accommodating a first substance, and a second chamber accommodating a second substance;

a biasing element disposed in the lower housing, and configured to move the upper housing and the lower housing apart from one another;

a needle in fluid communication with the at least one chamber and extending into the lower housing such that a distal end of the needle extends out of a distal end of the lower housing for injecting into the patient; and a barrier for isolating the second chamber from the first chamber, wherein the barrier may be compromised causing the first and second substances to mix in at least one of the first and second chambers, wherein the barrier is coupled to a sleeve by a coupling element that passes through the needle, and wherein movement of the sleeve dislodges the barrier thereby causing the first and second substances to mix for injection into the patient.

* * * * *